US007298487B2

(12) United States Patent
Hansen et al.

(10) Patent No.: US 7,298,487 B2
(45) Date of Patent: Nov. 20, 2007

(54) METHOD AND APPARATUS FOR MEASURING LIGHT REFLECTIONS OF AN OBJECT

(75) Inventors: Jan Harries Hansen, Lyngby (DK); Hans Ole Nielsen, Lyngby (DK); Kai Ove Sørensen, Lyngby (DK); Jesper Falden Offersgaard, Skovlunde (DK)

(73) Assignee: Delta Dansk Elektronik, Lys & Akustik, Horsholm (DK)

( * ) Notice: Subject to any disclaimer, the term of this patent is extended or adjusted under 35 U.S.C. 154(b) by 98 days.

(21) Appl. No.: 10/511,686

(22) PCT Filed: Apr. 2, 2003

(86) PCT No.: PCT/DK03/00222

§ 371 (c)(1),
(2), (4) Date: Oct. 13, 2004

(87) PCT Pub. No.: WO03/087792

PCT Pub. Date: Oct. 23, 2003

(65) Prior Publication Data

US 2005/0146725 A1 Jul. 7, 2005

(30) Foreign Application Priority Data

Apr. 15, 2002 (DK) ................ 2002 00561

(51) Int. Cl.
*G01N 21/55* (2006.01)
*G01N 21/47* (2006.01)

(52) U.S. Cl. .................. 356/445; 356/446

(58) Field of Classification Search .......... None
See application file for complete search history.

(56) References Cited

U.S. PATENT DOCUMENTS

| | | | | | |
|---|---|---|---|---|---|
| 3,527,913 | A | * | 9/1970 | Gionet | 200/559 |
| 4,250,538 | A | * | 2/1981 | Durbin et al. | 362/97 |
| 4,373,819 | A | * | 2/1983 | Pallotta | 356/445 |
| 4,422,758 | A | * | 12/1983 | Godfrey et al. | 356/152.1 |
| 4,721,389 | A | * | 1/1988 | Dejaiffe | 356/445 |
| 5,461,472 | A | * | 10/1995 | Harvey et al. | 356/138 |
| 5,699,164 | A | * | 12/1997 | Lehan et al. | 356/445 |
| 5,777,244 | A | * | 7/1998 | Kumagai et al. | 73/865.8 |
| 5,792,610 | A | * | 8/1998 | Witney et al. | 435/6 |
| 5,816,681 | A | * | 10/1998 | Tedesco | 362/459 |
| 5,839,812 | A | * | 11/1998 | Ge et al. | 362/607 |
| 5,929,987 | A | * | 7/1999 | Hayes | 356/337 |
| 6,166,813 | A | * | 12/2000 | Roberts | 356/445 |
| 6,212,480 | B1 | * | 4/2001 | Dunne | 702/159 |
| 6,407,674 | B1 | * | 6/2002 | Gallagher | 340/905 |
| 6,674,878 | B2 | * | 1/2004 | Retterath et al. | 382/104 |
| 2002/0186865 | A1 | * | 12/2002 | Retterath et al. | 382/104 |

FOREIGN PATENT DOCUMENTS

GB   2 110 416 A   11/1982
WO   WO97/27470   7/1997

OTHER PUBLICATIONS

Fundamentals of Optics, Fourth Edition, Jenkins and White, McGraw-Hill, 1976, Chapter 7, p. 115.*
Delta: "On site quality control of road markings & road surfaces in accordance with cEN specifications".

* cited by examiner

*Primary Examiner*—Gregory J. Toatley, Jr.
*Assistant Examiner*—Jonathan Skovholt
(74) *Attorney, Agent, or Firm*—Day Pitney LLP

(57) ABSTRACT

A method and apparatus for measuring light reflections of an object, comprising a light-source illumination-observation assembly, the assembly comprising: (A) an illumination unit comprising an illumination light source and illumination aperture stop being arranged to provide a confined luminous field, an illumination field stop (307) adapted to provide an illumination beam (305) of light from said confined luminous field, an collimating optical element (309) adapted to collimate said illumination beam and to provide an illumination field (313) on an object; (B) an observation unit comprising: at least one observation field stop adapted to provide an observation beam (306) comprising a ray boundary, at least one focusing optical element (309) adapted to focus said observation beam, an observation light receiver; and (C) at least one common optical element (309) arranged so that said illumination beam and said observation beam form an overlap therein; and (D) a unit separation stop (310) adapted to stop light from said illumination unit in reaching said observation light receiver of said observation unit; wherein said at least one observation field stops (308, 310, 311) comprises at least one limiting field stop (310) adapted to limit said ray boundary of said observation beam and to maintain said overlap of said illumination beam and said observation beam; a diffuser light-source assembly; and use thereof.

20 Claims, 6 Drawing Sheets

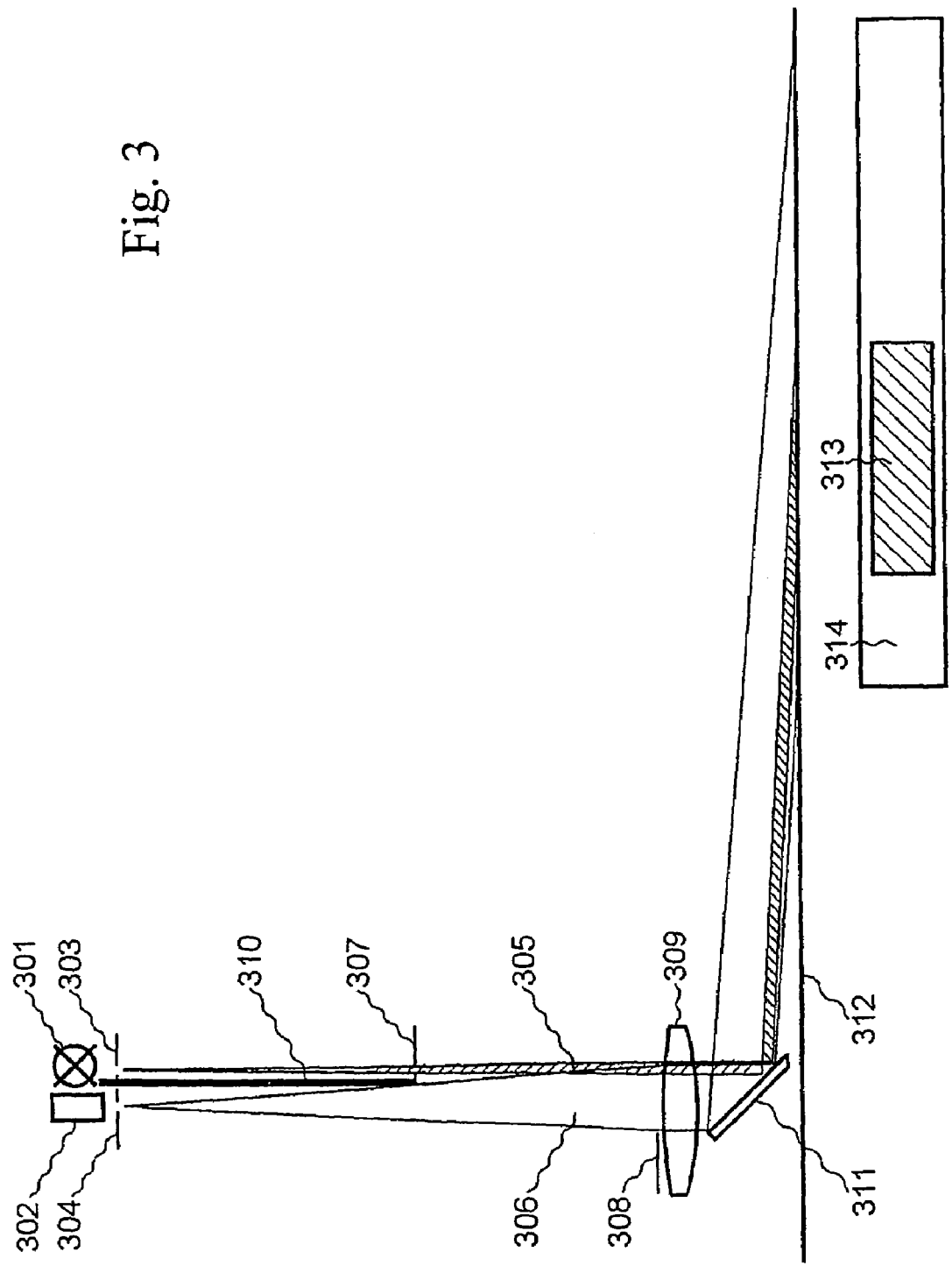

METHOD AND APPARATUS FOR MEASURING LIGHT REFLECTIONS OF AN OBJECT

BACKGROUND OF THE INVENTION

The present invention relates to a method of measuring light reflections of an object, a light-source illumination-observation assembly, a diffuser light-source assembly, an apparatus for measuring light reflections of an object comprising such a light-source illumination-observation assembly, such an apparatus further comprising a diffuser light-source assembly, and use of such an apparatus for measuring reflection, retroreflection, or both, preferably the object being a reflective material, a reflective device, a retroreflector material, and a retroreflector device, or a combination thereof, in particular a road marking, a road surface, a raised pavement marking, or all.

THE TECHNICAL FIELD

Road markings are typically provided by application of marking materials such as paint, thermoplastic materials, cold hardening materials, preformed lines, and symbols onto the surface of the road. Road marking materials can be applied with or without addition of colors, e.g. white, yellow, or other colors.

Road markings are often profiled to produce a certain surface textures to enhance special properties, e.g. for enhancing retroreflectivity under conditions of wet or rainy weather, or to produce a signal to the driver of a vehicle in the form of an acoustistic signal or vibration when crossed at speed.

In particular road markings may comprise addition of retro-reflective materials such as glass beads, in particular road markings intended for illumination by vehicle headlamp illumination.

The coefficient of retroreflected luminance $R_L$ (unit $mcd \cdot m^{-2} \cdot lx^{-1}$) is a characteristic measure for the retroreflection of road markings and road surfaces in vehicle headlamp illumination at night.

According to current European (CEN) and American (ASTM) standards, road marking performance is measured by the coefficient of retroreflected luminance, $R_L$, determined as the ratio between the retroreflected luminance L of a measured field of the road marking in the direction of observation by the illuminance $E_1$ at the measured field perpendicular to the direction of the incident light.

Illumination and observation are at specified geometrical conditions involving directions at predefined small angles relative to the surface of the road marking to be measured.

It depends on the marking material used, age and wear thereof. A high retroreflected luminance corresponds to a high level of visual performance.

Adequate visibility of road markings in night driving conditions is generally assured by minimum requirements for the $R_L$ values of the road markings. Requirements are included in national legislation and national road standards and serve as the basis for warranties and contracts.

The luminance coefficient under diffuse illumination $Q_d$ (unit $mcd \cdot m^{-2} \cdot lx^{-1}$) is a characteristic measure for the reflection of road markings and road surfaces in daylight and under road lighting. Adequate visibility of road markings in day driving conditions is generally assured by minimum requirements for the $Q_d$ values of the road markings. Requirements are included in national legislation and national road standards and serve as the basis for warranties and contracts.

For testing purposes, portable retroreflectometers and reflectometers are known for the measurement of the $R_L$ and $Q_d$ of road markings in situ conditions.

Illumination and observation involves particular illumination and observation fields on the surface of the road marking to be measured. In order to reduce influence of any misalignment of the retroreflectometer, when placed on a road for measuring under real conditions of debris and small particles on the road marking, or of texture, profiled road markings, or vertical curves of the road marking, either of the illumination field or the observation field is smaller than the other field and enclosed within that field, in particular the illumination field is chosen as the smaller of the two.

Consequently, there is a need for improved portable reflectometers that are compact, simple to manufacture, robust against misalignment in operation, and simple to use.

PRIOR ART DISCLOSURES

U.S. Pat. No. 4,721,389 discloses a method and apparatus for measuring retroreflectivity of a reflective layer on a surface, such as a roadway markings, said method and apparatus comprising steps and means for illuminating a portion of the reflective layer with a laser beam of a predetermined wavelength at an angle of incidence and steps and means for observing the reflected laser beam in an observation angle, filtering the observed reflected laser light, and detecting the filtered reflected laser light in a photometer.

American Society for Testing Materials, ASTM Designation: E1710-97, "Standard Test Method for Measurement of Retroreflective Pavement Marking Materials with CEN-prescribed Geometry Using a Portable Retroreflectometer" discloses a test method for measurement of retroreflective properties of horizontal pavement marking materials containing retroreflecting spheres.

European Committee for Standardization, CEN EN1436: 1997, "Road marking materials—road marking performance for road users" discloses standard specifications and test methods for the performance for road users of white and yellow road markings.

DISCLOSURE OF THE INVENTION

Object of the Invention

It is an object of the present invention to seek to provide an improved method and apparatus for measuring light reflections of an object.

In particular, it is an object of the present invention to seek to provide such an improved method and apparatus for measuring light reflections of road markings, in particular light retroreflection in headlamp illumination and light reflection under conditions prevailing during daylight and under road lighting.

It is still another object of the present invention to seek to provide such an improved method and apparatus for carrying out such measurements, in particular in a portable measuring apparatus for measuring retroreflection.

Further objects appear from the description elsewhere.

Solution According to the Invention

"Method for Measuring Light Reflections"

According to an aspect of the present invention there is a method comprising:
(A) providing an illumination beam, said illumination beam illuminating an illumination field on the object;
(B) providing an observation beam, said observation beam comprising light received from an observation field on said illuminated object; said observation beam comprising a ray boundary defined by an observation field stop; and said illumination beam and said observation beam being overlapping;
(C) providing a measuring signal from said observation beam in a light receiver; and
(D) determining a reflection coefficient from said measuring signal;

wherein said observation field stop comprises one or more field stops of which at least one field stop is a limiting field stop adapted to limit said ray boundary of said observation beam and to maintain said overlap of said illumination beam and said observation beam, whereby it is obtained that a maximum observation field can be obtained while maintaining an overlap between said illumination field and observation field, and that areas of optical elements can be effectively utilized.

In a preferred embodiment, said one or more observation field stops and said at least one limiting field stop are mutually displaced along the direction of propagation of said observation beam whereby the observation field stop can be optimized and areas of collimating optical elements can be effectively utilized.

"Light-Source Illumination-Observation Assembly"

According to another aspect of the present invention, there is provided a light-source illumination-observation assembly comprising:
(A) an illumination unit, said illumination unit comprising:
(a) an illumination light source, said illumination light source comprising at least one light source and an illumination aperture stop, said at least one light source and said illumination aperture stop being arranged to provide a confined luminous field,
(a) an illumination field stop, said illumination field stop being adapted to provide an illumination beam of light from said confined luminous field,
(b) an collimating optical element, said collimating optical element being adapted to collimate said illumination beam and to provide an illumination field on an object;
(B) an observation unit, said observation unit comprising:
(a) at least one observation field stop, said at least one observation field stop being adapted to provide an observation beam of light from an observation field on said object, said observation beam comprising a ray boundary;
(b) at least one focusing optical element, said at least one focusing optical element being adapted to focus said observation beam,
(c) an observation light receiver, said observation light receiver comprising a light receiver and an aperture stop, said light receiver and said observation aperture stop being arranged to provide a confined receiving field of said focused observation beam; and
(C) at least one common optical element, said at least one common optical element being arranged so that said illumination beam and said observation beam form an overlap therein; and
(D) a unit separation stop, said unit separation stop being adapted to stop light from said illumination unit in reaching said observation light receiver of said observation unit;

wherein said at least one observation field stops comprises at least one limiting field stop adapted to limit said ray boundary of said observation beam and to maintain said overlap of said illumination beam and said observation beam, whereby it is obtained that a maximum observation field can be obtained while maintaining an overlap between said illumination field and observation field, and that the area of the optical elements can be effectively utilized.

In a preferred embodiment, said at least one observation field stop and said at least one limiting field stop are mutually displaced along the direction of propagation of said observation beam whereby the observation field stop can be optimized and the area of the collimating optical element can be effectively utilized.

In a preferred embodiment, said unit separation stop is adapted to stop light reflections whereby false signals originated from both the illumination unit, or illumination channel, can be reduced.

In a preferred embodiment, said collimating optical element and said focusing optical element are accommodated in a single optical element whereby a particular simplified, robust, and compact assembly with a reduced number of components can be provided, e.g. in particular useful in a portable apparatus for measuring light retroreflection from road markings or road surfaces.

In a preferred embodiment, said collimating optical element is displaced off-axis so that its optical axis is substantially parallel to the optical axis of said observation aperture stop whereby the direction of reflections in the faces of the optical element can be adapted to avoid reaching the light receiver. Also, it is obtained that the central area of the collimating optical element can be used thereby avoiding using edges of e.g. a lens and reduced aberration effects.

In a preferred embodiment, said collimating optical element is tilted so that its optical axis is non-parallel to the optical axis of the said observation aperture stop whereby it is obtained that reflections from faces of the collimating optical elements reach the light receiver.

In a preferred embodiment, said unit separation stop comprises a wall; said illumination field stop being fixed to said wall whereby a particularly simple optical arrangement and easy to mount assembly is obtained.

In a preferred embodiment, the assembly further comprises a directional optical element for lateral direction of said collimated illumination beam whereby it is made easy to approach an apparatus incorporating the assembly against a large object such as a road and achieves large angles of incidence, i.e. the collimated illumination is close to the surface of the road.

In a preferred embodiment, said collimating optical element, said focusing element, said common optical element, and said directional optical element are selected from the group consisting of refractive optical elements, reflective optical elements, and diffractive optical elements, or a combination thereof whereby different optical techniques can be selected depending on the particular application.

In a preferred embodiment, said refractive optical element is a lens, lens assembly, prism, or a combination thereof whereby a simplified assembly can be provided.

In a preferred embodiment, said reflective optical element is a mirror, preferably a planar mirror or a non-planar mirror, or a combination thereof whereby a simplified assembly can be provided.

In a preferred embodiment, said diffractive optical element is a hologram whereby a particular compact apparatus can be provided.

In a preferred embodiment, said collimating optical element, said focusing element, said common optical element, and said directional optical element are accommodated in single element, said single element comprising a concave mirror, non-planar prism, or a hologram, or a combination thereof whereby a particular compact apparatus can be provided.

"Diffuser Light-Source Assembly"

According to another aspect of the present invention, there is provided a diffuser light-source assembly comprising:
(A) a light source; and
(B) a diffuser with a cavity wall, said diffuser comprising:
(a) a diffusive reflecting cavity wall, said diffusive reflecting cavity wall comprising partly or wholly reflective surface elements, providing multiple reflections of said light received through said light receiving aperture, and
(b) a plurality of light emitting apertures, said light emitting apertures being arranged in said cavity wall and being adapted to emit diffused light, whereby it is obtained that a simplified diffuser is obtained.

In a preferred embodiment, said light emitting apertures constituting less than 20%, preferable less than 10%, in particular 3% to 5% of said cavity wall whereby it is obtained that a sufficient number of reflections is achieved to ensure conditions of diffused light.

In a preferred embodiment, said diffuser cavity wall comprises a light receiving aperture said light receiving aperture being adapted to receive light from said light source whereby a simplified two-part cavity-light-source system for which the light source is easy to exchange can be obtained.

In a preferred embodiment, said reflective surface comprises a white finish applied to interior walls thereof whereby particular highly diffusive reflections of the cavity wall can be obtained.

In a preferred embodiment, said diffuser comprises a longitudinally extending cavity having a rectangular cross section, said cavity comprising an end face accommodating said light receiving aperture, and a bottom face accommodating said plurality of light emitting apertures whereby a simple and compact form of the diffuser can be obtained, in particular more compact in comparison with a normally used spherical diffuser in the art.

In a preferred embodiment, said cavity wall comprising said plurality of light emitting apertures consist of a thin perforated plate; the thickness of said plate being selected so that conditions of diffused light is maintained whereby a particularly simple and compact form of the diffuser can be obtained. Further it is ensured that the apertures do not significantly disturb the diffusive character of the emitted diffused light.

"Apparatus for Measuring Light Reflections"

According to another aspect of the present invention, there is provided an apparatus for measuring light reflections of an object comprising:
(a) a housing;
(b) a light-source illumination-observation assembly according to the invention incorporated in said housing.

According to still another aspect the apparatus further comprises a diffuser light-source assembly according to the invention.

Preferred embodiments are defined in the sub claims.

In a preferred embodiment, the apparatus further comprises means for determining a reflection coefficient of the measured reflection of the object where the physical measurements of received light is converted into meaning full numbers which are considered representative for the light reflection of the measured object.

In a preferred embodiment, the apparatus further comprising means for selecting a light source between said light source illumination-observation assembly and said diffuser light-source assembly whereby particular simple switching between the light sources used for the light retroreflection and reflection measurements can be obtained.

"Use of the Apparatus"

According to still another aspect the apparatus used for measuring light retroreflection, light reflection, or both whereby robust measurements against misalignments is obtained.

In a preferred embodiment, the apparatus according to the present invention is used for measuring light reflections of objects such as a reflective material, a reflective device, a retroreflector material, and a retroreflector device, or a combination thereof, in particular a road marking, a road surface, a raised pavement marking, or all.

BRIEF DESCRIPTION OF THE DRAWINGS

In the following, by way of examples only, the invention is further disclosed with detailed description of preferred embodiments. Reference is made to the drawings in which

FIG. 3 shows an illustration of an embodiment according to the invention;

DETAILED DESCRIPTION

"Prior Art"

Figure 1:
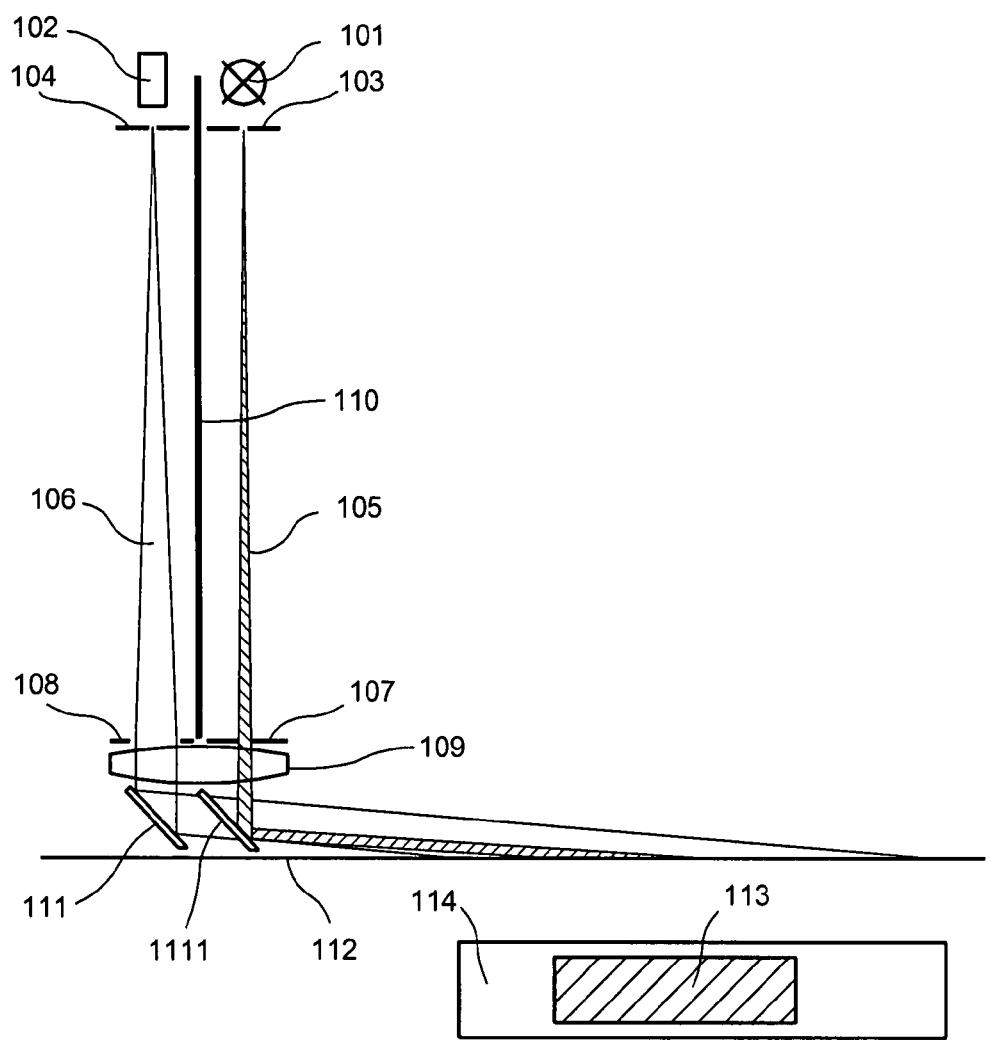
FIG. 1 shows an illustration of an apparatus for measuring light retroreflection according to prior art.

FIG. 1 shows an illustration of an apparatus for measuring light retroreflection according to prior art.

The optical arrangement of a portable retroreflectometer comprises two light channels, one for illumination and one for observation, separated by a wall 110 which wall reduce generation of "false" signals by preventing illumination light of the illumination channel in reaching the observation channel.

The illumination channel comprises a light source 101 emitting light through an illumination aperture stop 103 from which light propagates as an illumination beam 105 through an illumination field stop 107. The illumination beam is collimated by a collimating lens 109. A beam splitter 1111 reflects the collimated beam to provide an illumination field 113 on a surface 112 of a road marking or road surface on which the reflectometer is placed.

The observation channel comprises a mirror 111 reflecting light from an observation field 114 originated from the surface 112 and received through the beam splitter 1111 of the illumination channel. The collimating lens 109 focusses light reflected by the mirror 111. An observation field stop 108 defines an observation beam 106. A receiver 102 collects light of the observation beam through an observation aperture stop 104.

The observation field 114 comprises the illumination field 113.

Figure 2:
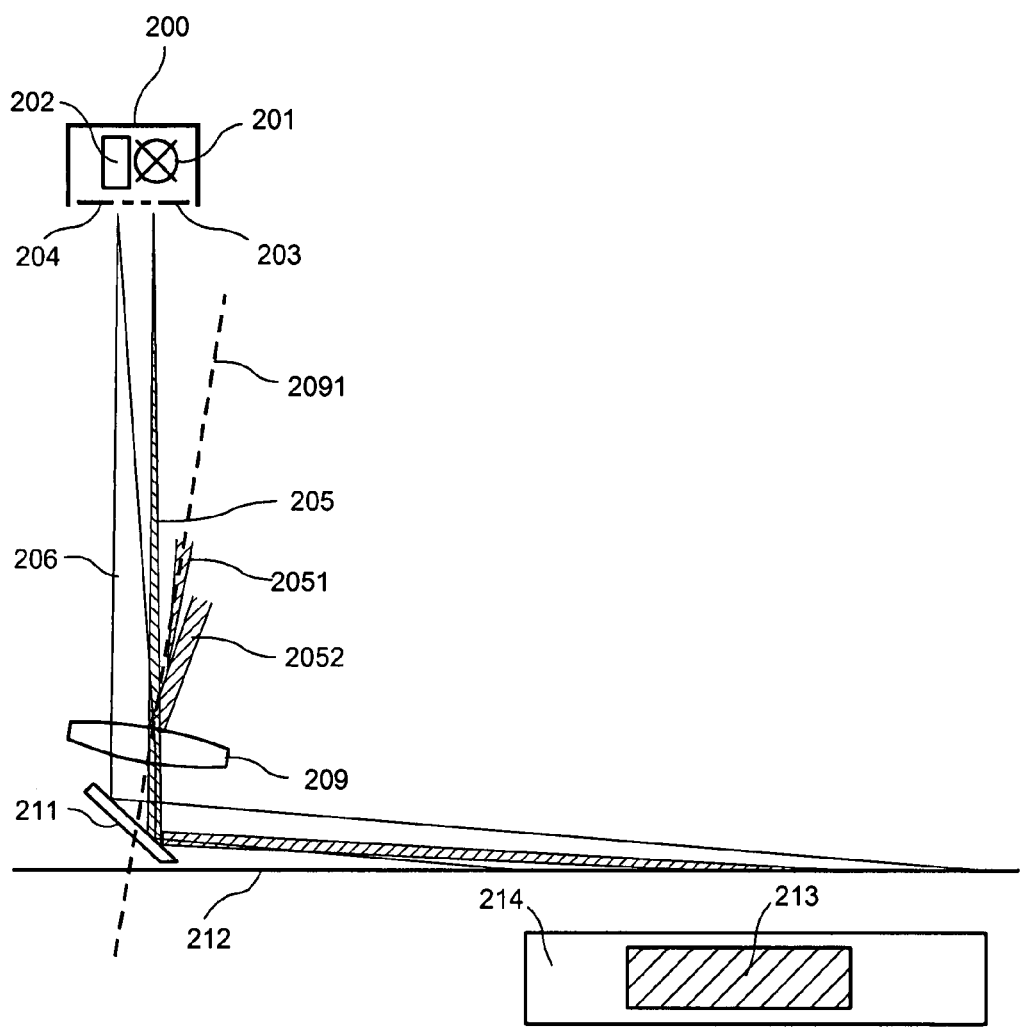
FIG. 2 shows another illustration of an apparatus for measuring light retroreflection according to prior art.

FIG. 2 shows another illustration of an apparatus for measuring light retroreflection according to prior art.

The optical arrangement of a portable retroreflectometer does not include a separation between channels for illumination and observation.

An illumination-receiver unit 200 comprises a light source 201, an illumination aperture stop 203, a receiver 202, an observation aperture stop 204 and optics, which define an illumination beam 205 and an observation beam 206, both with limited angular extensions in the same way as would have been the case using field stops.

The illumination beam 205 passes through a collimating lens 209. A mirror 211 reflects the collimated beam onto an illumination field 213 on the surface 212 of a road marking or road surface on which the reflectometer is placed. The mirror 211 reflects an observation beam 206 from an observation field 214 via the collimating lens 209, here functioning as a focusing lens, onto the receiving part of illumination-receiver unit 200.

The illumination field 213 is enclosed within the observation field 214.

This optical arrangement avoids a beam splitter and a consequent loss of effective measuring signal. A larger area of the collimating lens 209 can be used.

In order to shape the illumination and observation beams, additional optics is required in the illumination-receiver unit. Further, reflections of illumination light might reach the observation channel. In particular, a reflection of the illumination beam 205 in the lower lens surface 2051 and in the upper lens surface 2052 might reach the detector 202 and create false signals.

Such false signals can be avoided by tilting the collimating lens 209 which, however, makes the illumination beam 205 and the observation beam 206 pass the collimating lens 209 at a considerable larger angle to the lens axis 2091 at which the collimating property of the collimating lens is reduced.

EMBODIMENTS ACCORDING TO THE INVENTION

FIG. 3 illustrates an embodiment of an illumination-observation assembly according to the invention.

The illumination-observation assembly comprises: (A) an illumination channel, unit for illumination of an object, (B) an observation channel, or unit for observation of reflected light from the object, (C) an illumination-observation beam-overlapping common optical element, and (D) a unit separation stop for stopping light reflections from said illumination unit in reaching said observation light receiver of said observation unit.

The illumination unit comprises an illumination light source comprising at least one light source 301, e.g. a Super-Quiet Xenon Flash lamp from Hamamatsu or an 8 V 20 W halogen incandescent lamp type 64255 from Osram, and an illumination aperture stop 303, said at least one light source and said illumination aperture stop being arranged to provide a confined luminous field.

This can be accomplish in any suitable way, e.g. the luminous parts of the light source itself can define the confined luminous field, so that the aperture stop is not required. Other confined luminous fields includes an exit of an optical fibre, or the optical image of a luminous field of a different shape or size.

The non-stopped, transmitted light from said confined luminous field propagates in an illumination beam 305 defined by an illumination field stop 307.

The illumination unit further comprises a collimating optical element for collimating the illumination beam 305; here a collimating refractive optical element in form of a lens 309, e.g. a commonly available planar-convex lens of suitable diameter and focal length.

"Observation Unit/Channel"

Generally, the observation unit, or channel, comprises means for observation of all, or a part, of the illuminated field on the object.

The observation unit comprises at least one observation field stop (308, 310, 311), said at least one observation field stop being adapted to provide an observation beam 306 of light from an observation field 314 on said object, said observation beam comprising a ray boundary.

The at least one observation field stops comprises at least one limiting field stop 310 adapted to limit said ray boundary of said observation beam and to provide an overlap of said illumination beam and said observation beam.

The observation unit further comprises at least one focusing optical element, said at least one focusing optical element being adapted to focus said observation beam, here a collimating refractive optical element, in particular a lens 309.

The observation unit further comprises an observation light receiver, said observation light receiver comprising a light receiver 302, e.g. a S1336 photo detector from Hamamatsu, or a R1617 Multialkali Photocathode HeadOn Photomultiplier Tube from Hamamatsu, and an aperture stop 304, said light receiver and said observation aperture stop being arranged to provide a confined receiving field of said focused observation beam.

This can be accomplish in any suitable way, e.g. the receiving parts of the light receiver itself can define the confined receiving field, so that the aperture stop is not required. Other confined receiving fields includes an entrance of an optical fibre, or the optical image of a receiving field of a different shape or size.

Generally, the light receiver is adapted to the illumination light source. In an embodiment, a long pass absorbtion filter, e.g. an OG 590 from Schott, is used in the light path between the light source and the light receiver, preferably in front of the light receiver.

In a preferred embodiment, the observation field comprises the illumination field so that variations of the illumination field occur within the observation field whereby variations in the measuring signal, e.g. due to surface variations of the object, can be reduced.

In another preferred embodiment, the illumination field comprises the observation field "Common Optical Element"

The illumination-observation assembly further comprises at least one common optical element, said at least one common optical element being arranged to overlap said illumination beam and said observation beam, here said common optical element is the collimating lens 309.

"Unit Separation Stop"

The illumination-observation assembly further comprises a unit separation stop, or channel separation stop, here a wall 310 that prevents light from the illumination channel or other light sources to enter into the observation channel thereby avoiding and/or reducing generation of false signals.

Generally, the unit separation stop is adapted to stop light from the illumination channel, e.g. either direct light or indirect light from light reflections, in reaching the light receiver of the observation channel. Further the unit separation stop does not influence the extent of the observation field defined with respect to the illumination field.

It is preferred that said unit separation stop is adapted to stop light reflections, including stopping light reflections from unwanted external light source as well as reflections from the illumination unit.

In a preferred embodiment the unit separation stop comprises a wall 310, preferably coated with a light absorbing material, e.g. NEXTEL Velvet-Coating from 3M.

Generally, the illumination field stop 307 is placed at a suitable position between the illumination light source and the collimating optical element 309.

Consequently, in a preferred embodiment, the illumination field stop 307 is fixed to said wall.

In a preferred embodiment, this position is about half the way there between.

In a preferred embodiment, the wall function as said limiting observation field stop, in particular the end of said wall.

It is within the skills of a skilled person to assess the optimal position of the wall e.g. by use of ray tracing techniques known to a skilled person and calculation of the exact position for a given lens 309 and mirror 311.

"Lateral Directional Optical Element"

In a preferred embodiment, the illumination-observation assembly further comprising a directional optical element, here a reflective optical element in form of a mirror 311, e.g. a commonly available front-coated planar mirror, for lateral direction of said collimated illumination beam.

In this embodiment, also, the mirror 311 reflects the light originated from the observation field 314, generating said observation beam 306.

In applications of road marking measurements, the mirror is adapted to provide an illumination field on a surface 312 of a road or on the surface of a road marking at a predefined angle of incidence, here typically an angle of incidence prescribed by an international standard; e.g. ASTM E 1710-97 prescribing an entrance angle (illumination angle) of 88.76 degrees corresponding to a co-entrance angle (measured between the direction of illumination and the plane of the surface to be measured) of 1.24 degrees and an observation angle (measured between the directions of illumination and observation) of 1.05 degrees for determining the coefficient of retroreflected luminance of horizontal coating materials used in pavement markings.

"Off-axis Optical Element"

Figure 4A:
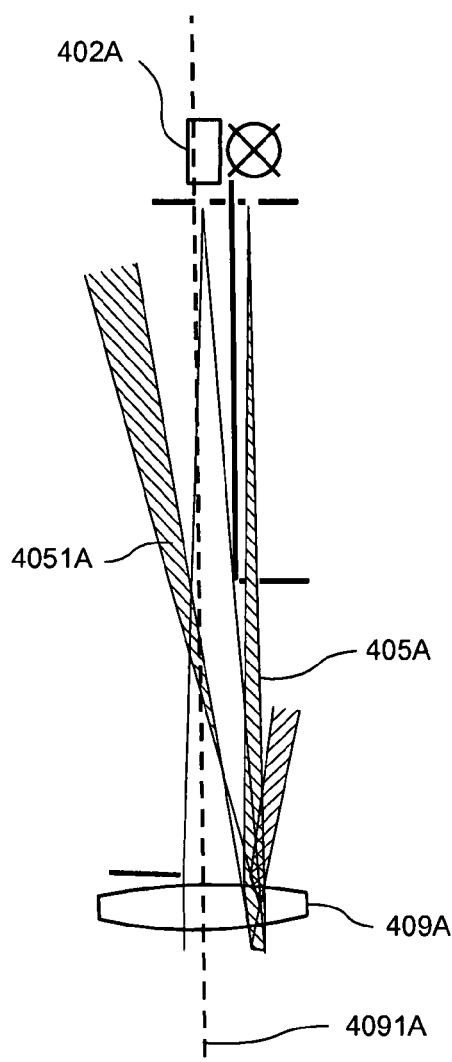
FIGS. 4a and 4b illustrate preferred embodiments of the illumination-observation assembly.

FIG. 4a illustrates a preferred embodiment of the illumination-observation assembly whereby it is avoided that reflection beams 4051A of an illumination beam 405A in the lower and upper surfaces of an off-axis collimating optical element 409A reaches the light receiver 402A.

The collimating optical element 409A is displaced so that its optical axis 4091A is not centred in the observation aperture stop whereby it is obtained that reflected beams 4051A pass on either side of the receiver 402A.

"Tilted Optical Element"

Figure 4B:
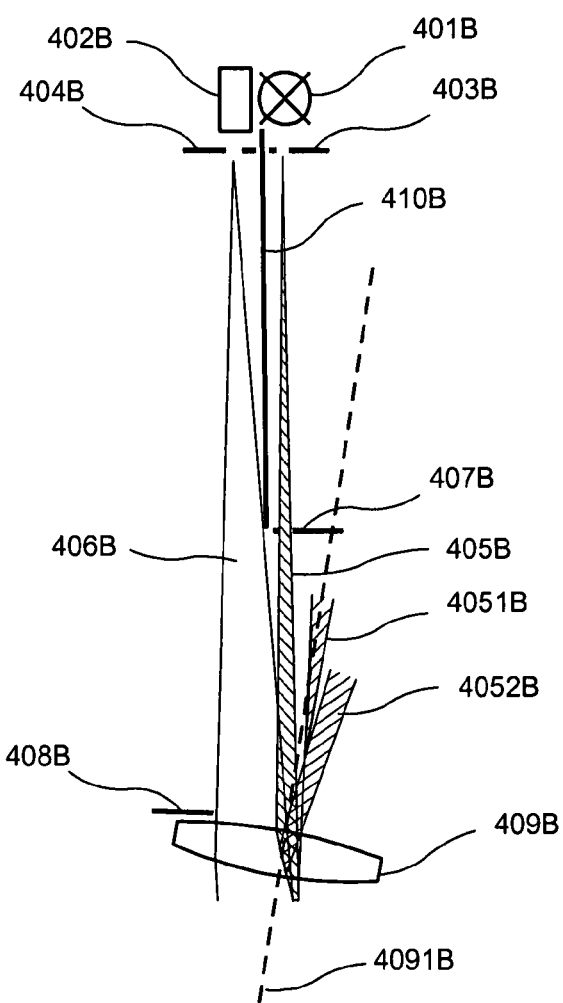

FIG. 4b illustrates another preferred embodiment of the illumination-observation assembly whereby it is avoided that reflection beams 4051B and 4052B of an illumination beam 405B in the lower and upper surfaces of a tilted optical element, here a collimating lens 409B reaches the light receiver 402B.

The collimating lens 409B is tilted so that reflected beams 4051B and 4052B pass on the same side of the receiver 402B.

Generally, the off-axis arrangement of FIG. 4a is preferred to lens tilting of FIG. 4b, as reduction of collimating property of a collimating lens 409A by a displacement is insignificant compared to the reduction caused by tilting of a collimating lens 409B.

"Reduction of False Signals"

The optical arrangement is enclosed in a housing (not shown), which provides structural support of the instrument and reduction of false signal from ambient light, in particular daylight.

Further reduction of false signal from ambient light can be obtained by a two step measuring and calibration procedure known in the art, see description below.

Additional reduction of false signal may be obtained by use of a flash light source, whose illumination for a short measuring period includes a flash that dominates over even full daylight.

In the optical arrangement of FIG. 3, the collimating design does not involve a beam splitter as is the case with prior art; similar to the collimating optics illustrated in FIG. 1b of ASTM E 1710-97 for a portable road marking apparatus wherein a beam splitter is avoided.

An advantage of this optical arrangement is avoidance of a beam splitter and the consequent loss of effective measuring signal and reduced use of the collimating lens 309 as in prior art shown in FIG. 1.

An additional advantage is avoidance of additional optics in order to shape the illumination and observation beams as in prior art shown in FIG. 2.

The position of the illumination field stop 307 in a position above the lens cause the illuminated field 313 to become slightly less sharp, but not to an extent that has any significant influence on the performance of the apparatus according to the invention.

The partly separation between the two channels by a wall 310 extending part of the way down to the collimating lens 309 ensures adequate prevention of spill over of light from the illumination into the observation channel.

A large signal and a large observation field is obtained with a simple optical arrangement without any significant disadvantage.

In order to eliminate completely the influence of light penetrating from the illumination to the observation channel, the calibration of the apparatus includes a "zero calibration". A measurement is performed into a light trap of virtually no reflection, or into open air with a sufficient distance to objects, and the reading is adjusted to zero. After this, calibration is done by measurement of a calibration standard with a known light retroreflection value, and the reading is set to this value. The user is guided through this procedure in an automated sequence.

After calibration the apparatus is ready for measurement. The procedure includes a measurement of any ambient signal, and subtraction of this signal. For improved performance, the output of the light source is monitored independently, all in an automated procedure.

"Diffuser Light-source Assembly"

Figure 5:
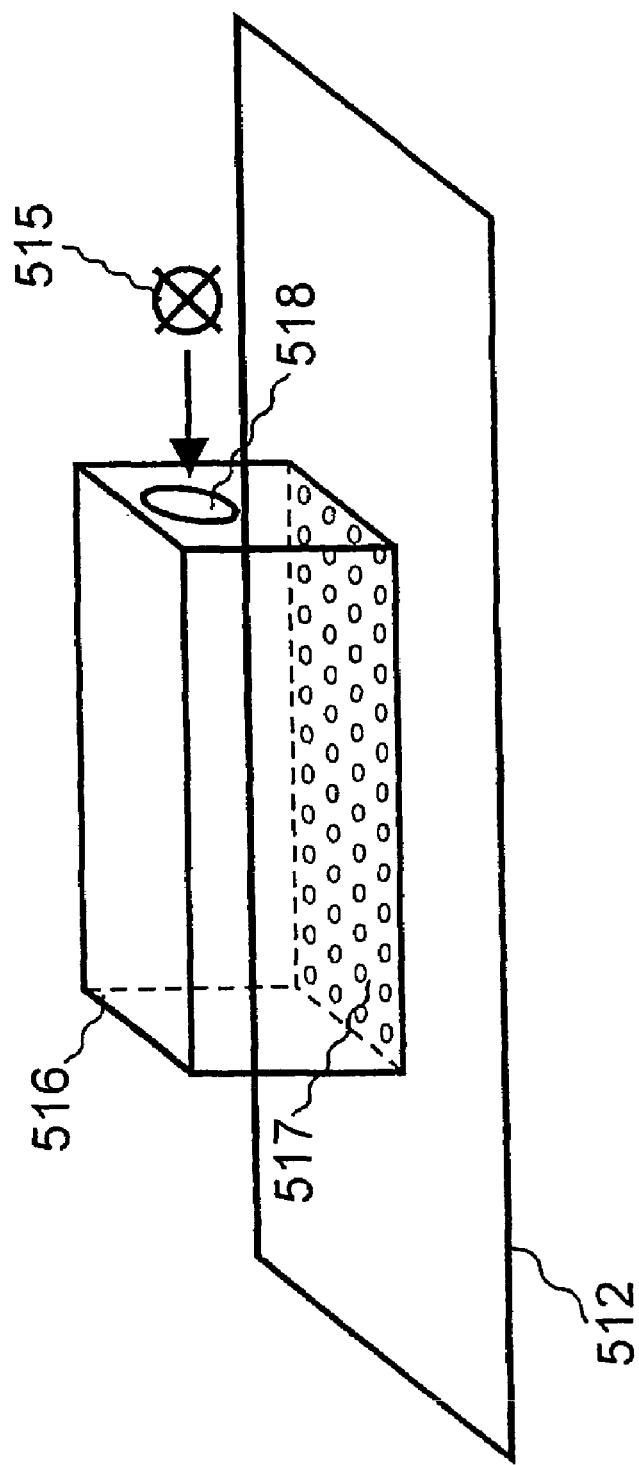
FIG. 5 shows an illustration of an embodiment of a diffuser light-source assembly according to the invention.

FIG. 5 shows an illustration of an embodiment of a diffuser light-source assembly according to the invention; here a diffuser 516 and a light source 515 combination.

In another embodiment the light source is integrated in the diffuser, preferably in the cavity wall.

The diffuser light-source assembly comprises a light source 515, e.g. a Super-Quiet Xenon Flash lamp from Hamamatsu or an 8 V 20 W halogen incandescent lamp type 64255 from Osram; and a diffuser 516, said diffuser comprising: a diffusive reflecting cavity wall 510, said diffusive reflecting cavity wall comprising partly or wholly reflective surface elements, providing multiple reflections of said light received through said light receiving aperture.

Further, said diffuser comprises a plurality of light emitting apertures 517, said light emitting apertures being arranged in said cavity wall and being adapted to emit diffused light.

The diffuser comprises a wall having a reflective interior surface, e.g. in form of a white finish applied to interior walls thereof. The reflective interior surface provides multiple reflections of light received therein thereby on average creating an essentially uniform luminance over the interior surface of the diffuser.

Further, the diffuser comprises means for receiving light from said light source, here an aperture in the wall thereof, e.g. an aperture in a side face of the diffuser.

Still further, the diffuser comprises means for emitting diffused light, here a plurality of apertures 517 arranged in the wall thereof, e.g. in form of a thin perforated plate 517 arranged as a bottom face of the diffuser, the thickness of the plate being selected so that conditions of diffused light is maintained.

In operation, the diffuser light source is positioned at a height above the surface of a road, in particular a road marking 512, which ensures conditions of diffused illumination—not necessary in each point of the illuminated surface—but on average.

"Apparatus for Measuring Light Reflections of an Object"

Figure 6:
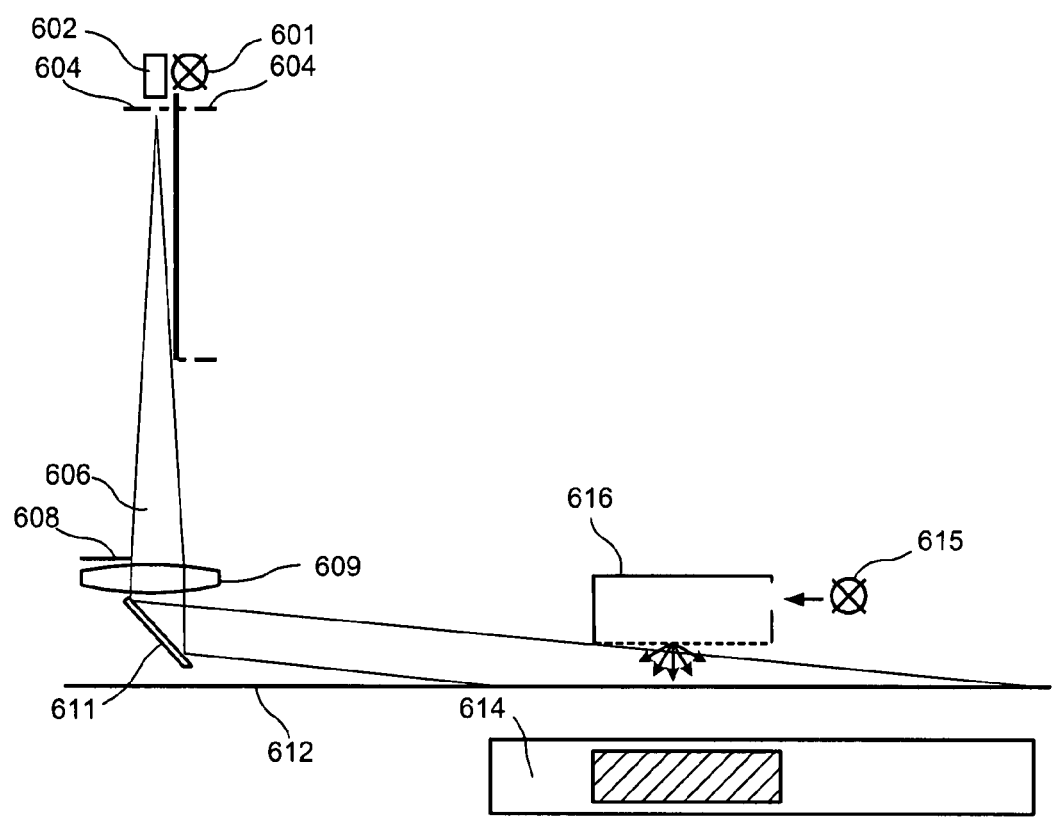
FIG. 6 shows an illustration of an embodiment of an apparatus for measuring light reflections of an object according to the invention.

FIG. 6 shows an illustration of an embodiment of an apparatus for measuring light reflections of an object, said apparatus comprising housing and a light-source illumination-observation assembly.

Further, the apparatus comprises a diffuser light-source assembly comprising a diffuser cavity 616 and a light source, here an external light source 615 according to the invention.

The apparatus further comprises means for determining a reflection coefficient of the measured reflection of the object, e.g. retroreflection measurements providing RL values.

The diffuser cavity 616 is positioned so that it is as close to the surface of the road marking 612 on which the reflectometer is placed, as possible, without obstructing the observation beam 606, and so that the illumination from the diffuser cavity 616 falls within the observation field 614.

In this embodiment the apparatus has two light sources, one light source for light retroreflection measurement 601 and an additional light source 615 for light reflection measurement by illumination of the diffuser cavity 616.

The observation channel functions so that the receiver 602 collects light from the observation beam 606 via the observation aperture stop 604. The collimating lens 609 collimates the light originated from an observation field 614 of the surface 612 and reflected by the mirror 611.

With the normal light source for light retroreflection measurement 601 turned on and the additional light source 615 turned off, the apparatus measures the light retroreflection of the road marking.

With the light source for light retroreflection measurement 601 turned off and the additional light source (615) turned on, the apparatus measures the light reflection of the road marking. In an automated sequence, the apparatus measures and displays both values.

Automated procedures are used for calibration as well as for measurement.

In a preferred embodiment, the illumination-observation assembly sketched in FIG. 3 is incorporated in a portable reflectometer for measurement of road markings and road surfaces.

"Calibration Procedure—Night Light/Daylight"

In order to eliminate completely the influence of light penetrating from the illumination to the observation channel, the calibration of the apparatus includes a "zero calibration" and a calibration for both types of measurement as described in the section "Reduction of false signals".

"Object and Applications"

Generally, the apparatus according to the present invention is used for measuring light retroreflection, light reflection, or both.

In a preferred embodiment, the apparatus according to the present invention is used for measuring light reflections of objects such as a reflective material, a reflective device, a retroreflector material, and a retroreflector device, or a combination thereof, in particular a road marking, road marking, a raised pavement marking, or all.

The invention claimed is:

1. An apparatus for measuring light reflections of an object, the apparatus comprising:
   (A) an illumination unit for providing an illumination beam (305), said illumination beam illuminating an illumination field (313) on the object;
   (B) an observation unit for providing an observation beam (306), said observation beam comprising light received from an observation field on said illuminated object; said observation unit comprising at least a first observation field stop (310) adapted to define a ray boundary of said observation beam (306);
   the observation unit further comprising an observation light receiver (302, 304) adapted to provide a measuring signal for determining a reflection coefficient from said measuring signal;
   wherein the apparatus comprises a lens (309) common to the illumination unit and the observation unit;
   characterized in
   that said lens is arranged so that said illumination beam and said observation beam form an overlap therein;
   that the illumination unit and the least first observation field stop are configured to cause the observation field and the illumination field to have different sizes; and
   that said first observation field stop (310) comprises a wall member extending from the observation light receiver towards said lens; wherein the wall member extends only a part of the distance between the observation light receiver and the lens as to limit said ray boundary of said observation beam while maintaining said overlap of said illumination beam and said observation beam inside the lens.

2. The apparatus according to claim 1, comprising a second observation field stop (308) between the observation light receiver and the lens and displaced along the direction of propagation of said observation beam from the first observation field stop.

3. The apparatus according to claim 1 or 2, wherein said illumination unit comprises:
(a) an illumination light source, said illumination light source comprising at least one light source (301) and an illumination aperture stop (303), said at least one light source and said illumination aperture stop being arranged to provide a confined luminous field,
(b) an illumination field stop (307), said illumination field stop being adapted to provide the illumination beam (305) of light from said confined luminous field,
(c) a collimating optical element (309), said collimating optical element being adapted to collimate said illumination beam and to provide the illumination field (313) on the object;
wherein said observation unit comprises:
at least one focusing optical element (309), said at least one focusing optical element being adapted to focus said observation beam,
wherein the observation light receiver comprises a light receiver (302) and an observation aperture stop (304), said light receiver and said observation aperture stop being arranged to provide a confined receiving field of said focused observation beam;
wherein said first observation field stop is adapted to stop light from said illumination unit in reaching said observation light receiver of said observation unit.

4. The apparatus according to claim 1 or 2, wherein said first observation field stop (310) extends substantially half the distance between the observation light receiver and the lens.

5. The apparatus according to claim 1 or 2, wherein said first observation field stop is adapted to stop light reflections.

6. The apparatus according to claim 3, wherein said collimating optical element (309) and said focusing optical element (309) are accommodated in said lens (309).

7. The apparatus according to claim 3, wherein said collimating optical element (409A) has an optical axis which is displaced relative to the optical axis of said observation aperture stop (304).

8. The apparatus according to claim 3, wherein said collimating optical element (409B) is tilted so that its optical axis is non-parallel to the optical axis of the said observation aperture stop (404B).

9. The apparatus according to claim 3, wherein said illumination field stop (307) is fixed to said wall member.

10. The apparatus according to claim 3, further comprising a directional optical element (311) for lateral direction of said collimated illumination beam.

11. The apparatus according to claim 10, wherein said collimating optical element, said focusing element, and said directional optical element are selected from the group consisting of refractive optical elements, reflective optical elements, and diffractive optical elements, or a combination thereof.

12. The apparatus according to claim 11 wherein said refractive optical element is a lens, lens assembly, prism, or a combination thereof.

13. The apparatus according to claim 11 wherein said reflective optical elements is a mirror, preferably a planar mirror or a non-planar mirror, or a combination thereof.

14. The apparatus according to claim 3, the apparatus comprising:
a housing accommodating said illumination unit and said observation unit.

15. The apparatus according to claim 14 further comprising a diffuser light-source assembly (614, 615).

16. The apparatus according to claim 14 or 15 further comprising means for determining a retroreflection coefficient and/or a reflection coefficient of the measured light reflections of the object.

17. The apparatus according to claim 15, further comprising means for selecting a light source between said illumination unit and said diffuser light-source assembly.

18. A method of measuring at least one of light retroreflection and light reflection, the method comprising:
providing an apparatus for measuring light reflections of an object as defined in claim 1;
directing an illumination beam generated by said apparatus toward an observation field of an object;
receiving by said apparatus an observation beam from an observation field of said object so as to measure light reflections by the object; and
determining at least one of a retroreflection and a reflection coefficient of the measured light reflection of the object.

19. The method according to claim 18, wherein the object is chosen from the group consisting of a reflective material, a reflective device, a retroreflector material and a retroreflector device.

20. The method according to claim 18 wherein the object is chosen from the group consisting of a road marking, a road surface, and a raised pavement marking.

* * * * *